US008433526B2

United States Patent
Roy et al.

(10) Patent No.: US 8,433,526 B2
(45) Date of Patent: Apr. 30, 2013

(54) METHOD AND SYSTEM FOR STEAM QUALITY MONITORING

(75) Inventors: Binayak Roy, Guilderland, NY (US); Tao Guo, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 356 days.

(21) Appl. No.: 12/945,680

(22) Filed: Nov. 12, 2010

(65) Prior Publication Data
US 2012/0123696 A1 May 17, 2012

(51) Int. Cl.
*G06F 19/00* (2006.01)
(52) U.S. Cl.
USPC ............. 702/24; 702/85; 73/597; 73/64.53; 250/227.23; 250/339.1; 250/339.06; 250/227.11; 250/575; 250/573; 250/574; 356/336; 356/342; 356/328; 356/338; 48/101; 48/197 R
(58) Field of Classification Search ............ 702/24, 702/85; 73/861.06, 29.01, 597, 599, 64.53; 250/227.3, 222.2, 339.1, 339.06, 227.11, 250/343, 239, 345, 575, 351, 216, 215, 352, 250/573, 574; 356/336, 342, 484, 335, 328, 356/28.5, 343, 341, 227, 339, 338, 37, 72; 48/101, 197 R
See application file for complete search history.

(56) References Cited

U.S. PATENT DOCUMENTS

| | | | | |
|---|---|---|---|---|
| 4,135,387 A * | 1/1979 | Benedict | ............... | 73/64.53 |
| 4,137,462 A * | 1/1979 | Wyler | ............... | 250/573 |
| 4,295,368 A * | 10/1981 | Jannone | ............... | 374/54 |
| 4,497,577 A * | 2/1985 | Sato et al. | ............... | 356/336 |
| 4,862,001 A * | 8/1989 | Dowling et al. | ............... | 250/345 |
| 5,383,024 A * | 1/1995 | Maxey et al. | ............... | 356/336 |
| 5,470,749 A * | 11/1995 | Djabbarah et al. | ............... | 436/38 |
| 5,621,669 A * | 4/1997 | Bjornsson | ............... | 702/85 |
| 6,128,079 A * | 10/2000 | McCloskey et al. | ............... | 356/338 |
| 6,660,995 B1 * | 12/2003 | Canpolat et al. | ............... | 250/227.23 |
| 7,034,302 B2 * | 4/2006 | Davidson et al. | ............... | 250/339.1 |

(Continued)

FOREIGN PATENT DOCUMENTS
JP 2009275656 A 11/2009

OTHER PUBLICATIONS

Walters, P.T., "Wetness and Efficiency Measurements in L.P. Turbines with an Optical Probe as an Aid to Improving Performance," Jan. 1987, vol. 109, Issue 1, pp. 85-92 (7 pages).

(Continued)

*Primary Examiner* — Carol Tsai
(74) *Attorney, Agent, or Firm* — Fletcher Yoder, P.C.

(57) ABSTRACT

A method of determining a steam quality of a wet steam located in an interior of a steam turbine includes emitting from an optical probe a plurality of wavelengths through the wet steam, measuring with the optical probe a wet steam intensity corresponding to each of the plurality of wavelengths emitted through the wet steam, determining an intensity ratio vector by dividing the wet steam intensity by a corresponding dry steam intensity for each of the plurality of wavelengths, successively applying scaling factors to the intensity ratio vector to obtain a scaled intensity ratio vector, calculating a suitable value for each of the scaling factors to obtain a plurality of residuals, determining a minimum residual of the plurality of residuals, determining a droplet size distribution by calculating the droplet number density corresponding to the minimum residual, and determining the steam quality based on the droplet size distribution.

20 Claims, 7 Drawing Sheets

U.S. PATENT DOCUMENTS

| | | | | |
|---|---|---|---|---|
| 7,345,280 B2* | 3/2008 | Mitra et al. | ............... | 250/345 |
| 7,381,954 B2* | 6/2008 | Banerjee et al. | ............ | 250/339.1 |
| 7,638,070 B2* | 12/2009 | Johnson et al. | ............... | 252/373 |
| 8,100,580 B2* | 1/2012 | Hannula et al. | ............... | 374/42 |
| 2004/0056197 A1* | 3/2004 | Davidson et al. | .......... | 250/339.1 |

OTHER PUBLICATIONS

Partin, J.K., et al, "Development of Optical Technologies for Monitoring Moisture and Particulate in Geothermal Steam," Aug. 2006; Idaho National Laboratory (34 pages).

He, G. et al., "Study of the Method of Steam Wetness Measuring by Laser Scattering Devices," Jul. 29-31, 2008, International Conference on Advanced Infocomm Technology '08, Shenzhen, China (5 pages).

Cai, X, et al, "Investigation of wet steam flow in a 300 MW direct air-cooling steam turbine. Part 1: measurement principles, probe, and wetness," Mar. 19, 2009, College of Power Engineering, University of Shanghai for Science & Technology, Shanghai, People's Republic of China, pp. 625-634 (10 pages).

* cited by examiner

METHOD AND SYSTEM FOR STEAM QUALITY MONITORING

BACKGROUND OF THE INVENTION

The subject matter disclosed herein relates to steam monitoring systems and, more particularly, to systems and methods for steam quality monitoring and determination of droplet size distribution.

Steam is used in a wide range of applications covering many industries, such as heat transfer, power generation, and transportation. For example, steam may be used as a motive force in a steam turbine to convert thermal energy into rotary energy. A steam quality requirement, which may correspond to a moisture content of the steam, varies depending on the application. For example, steam turbines may require a high steam quality because a low steam quality may cause reduced efficiency and/or erosion of steam turbine components. Existing steam quality monitoring instruments typically use optical signals. Unfortunately, the accuracy of existing steam quality monitoring instruments may be negatively affected because of the effects of large water droplets on optical signals. Therefore, there is a need for an improved steam quality monitoring system to address one or more of the aforementioned issues.

BRIEF DESCRIPTION OF THE INVENTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, a method of determining steam quality of wet steam located in an interior of a steam turbine is provided. The method includes emitting from an optical probe a plurality of wavelengths through the wet steam, measuring with the optical probe a wet steam intensity corresponding to each of the plurality of wavelengths emitted through the wet steam, determining an intensity ratio vector by dividing the wet steam intensity by a corresponding dry steam intensity for each of the plurality of wavelengths, successively applying scaling factors to the intensity ratio vector to obtain a scaled intensity ratio vector, calculating a suitable value for each of the scaling factors to obtain a plurality of residuals, determining a minimum residual of the plurality of residuals, determining a droplet size distribution by calculating the droplet number density corresponding to the minimum residual, and determining the steam quality based on the droplet size distribution.

In a second embodiment, one or more non-transitory tangible machine-readable media comprising executable instructions are provided. The executable instructions, when executed by a processor, cause the processor to perform acts including measuring with an optical probe a wet steam intensity corresponding to each of a plurality of wavelengths emitted through a wet steam, determining an intensity ratio vector by dividing the wet steam intensity by a corresponding dry steam intensity for each of the plurality of wavelengths, successively applying scaling factors to the intensity ratio vector to obtain a scaled intensity ratio vector, calculating a suitable value for each of the scaling factors to obtain a plurality of residuals, determining a minimum residual of the plurality of residuals, determining a droplet size distribution by calculating the droplet number density corresponding to the minimum residual, and determining a steam quality based on the droplet size distribution.

In a third embodiment, a steam quality monitoring system is provided. The system includes an optical emitter configured to emit light at a plurality of wavelengths, an optical detector configured to detect light at the plurality of wavelengths, and a processor coupled to the optical emitter and the optical detector. The processor is configured to execute instructions stored in a memory or storage device. The instructions, when executed by the processor, cause the processor to perform acts including detecting with the optical detector a wet steam intensity corresponding to each of the plurality of wavelengths emitted by the optical emitter through the wet steam, determining an intensity ratio vector by dividing the wet steam intensity by a corresponding dry steam intensity for each of the plurality of wavelengths, successively applying scaling factors to the intensity ratio vector to obtain a scaled intensity ratio vector, calculating a suitable value for each of the scaling factors to obtain a plurality of residuals, determining a minimum residual of the plurality of residuals, determining a droplet size distribution by calculating the droplet number density corresponding to the minimum residual, and determining a steam quality based on the droplet size distribution.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Figure 1:
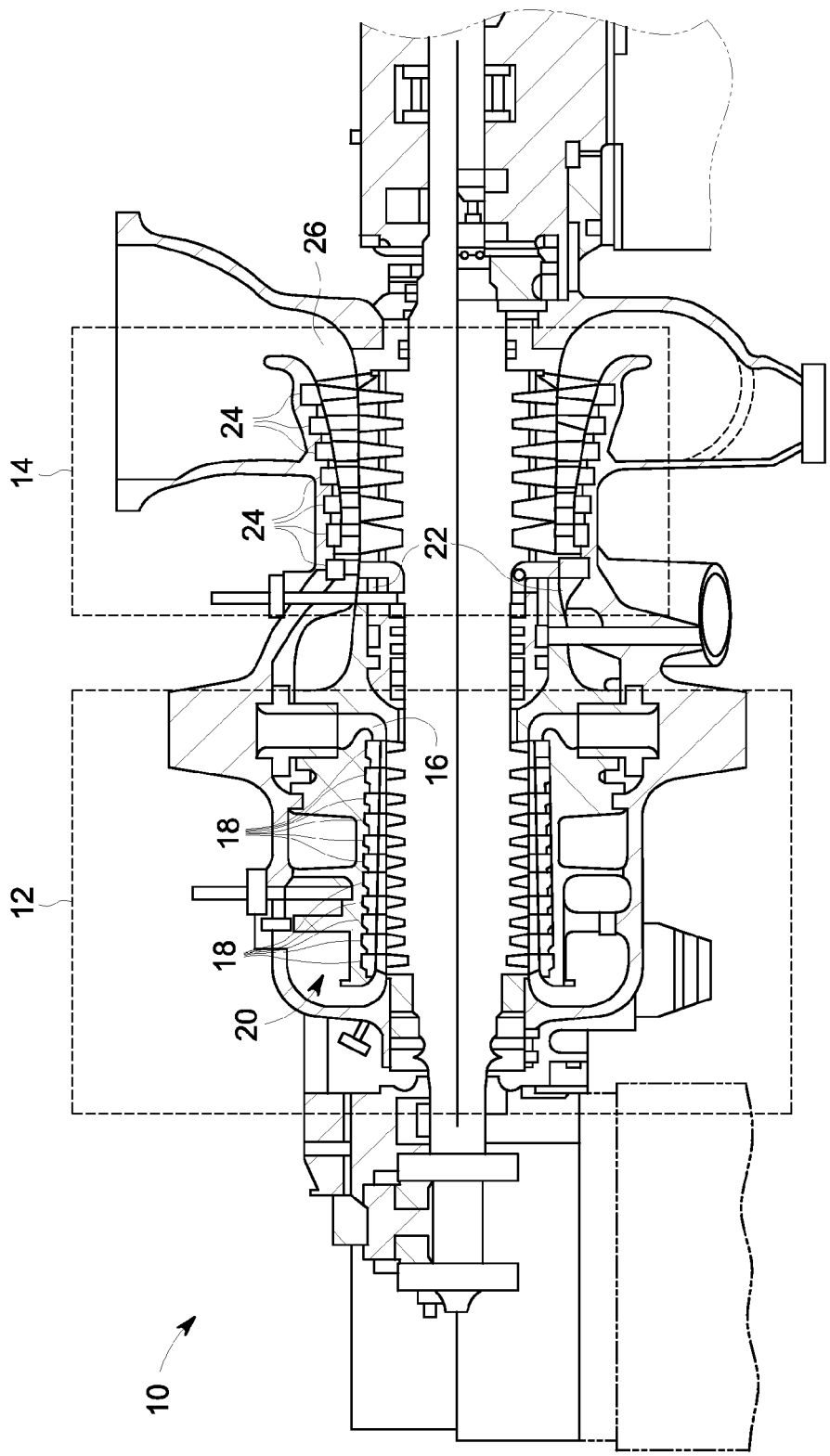
FIG. 1 is a cross-section of an embodiment of a steam turbine having multiple turbine stages.

FIG. 1 is a cross-sectional side view of a steam turbine 10 having a high-pressure section 12 and a low-pressure section 14. The steam turbine 10 may be used wherever steam is available for power generation, such as in coal plants, gasification plants, natural gas plants, nuclear plants, and so forth. The steam turbine 10 may include an embodiment of a steam quality monitoring system as described in detail below. During operation, a high-pressure steam inlet 16 receives high-pressure steam and routes the high-pressure steam through high-pressure turbine stages 18, driving turbine blades to cause rotation of a common rotor shaft of the steam turbine 10. An example of a source of the high-pressure steam includes, but is not limited to, a heat recovery steam generation (HRSG) system of an integrated gasification combined cycle (IGCC) power plant. The high-pressure steam exits the high-pressure section 12 of the steam turbine 10 through a high-pressure steam outlet 20. In certain embodiments, the high-pressure steam may be directed back to the HRSG system for further superheating and ultimate use in the low-pressure section 14 of the steam turbine 10.

Similarly, the low-pressure steam inlet 22 receives low-pressure steam, such as from the HRSG system, and routes the low-pressure steam through low-pressure turbine stages 24, driving blades to cause rotation of the common rotor shaft of the steam turbine 10. The low-pressure steam exits the low-pressure section 14 of the steam turbine 10 through a low-pressure steam outlet 26. In certain embodiments, the steam turbine 10 may also include an intermediate-pressure section.

The steam turbine 10 may include one or more optical probes used to determine a steam quality of wet steam located in an interior of the steam turbine 10 as described in detail below. In various embodiments, the optical probes may be disposed in locations throughout the interior of the steam turbine 10. For example, the optical probes may be disposed in the high-pressure section 12, the low-pressure section 14, or the intermediate-pressure section (if present). In other embodiments, the optical probes may be placed wherever measurement of the steam quality in the interior of the steam turbine 10 is desired.

Figure 2:
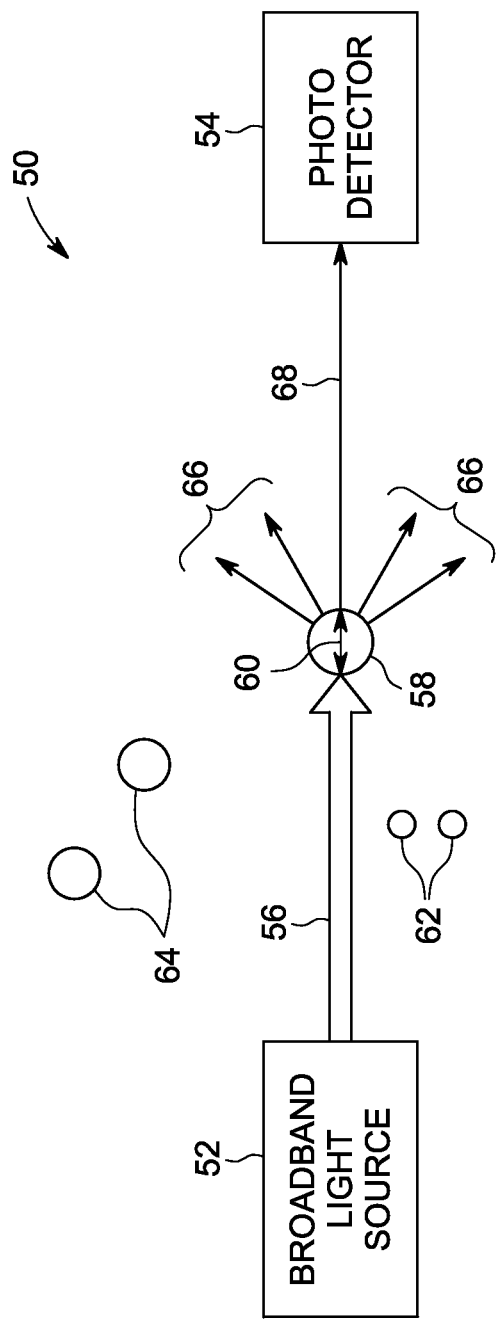
FIG. 2 is a schematic view of an embodiment of a steam quality monitoring system.

FIG. 2 is a schematic view of a steam quality monitoring system 50. In the illustrated embodiment, the monitoring system 50 includes an optical emitter 52 and an optical detector 54, which together may be referred to as an optical probe. Both the optical emitter 52 and the optical detector 54 may be coupled to interior stationary surfaces of the steam turbine 10. In addition, the optical detector 54 is typically configured opposite from the optical emitter 52. The optical emitter 52 is configured to emit light 56 at one or more wavelengths. For example, the one or more wavelengths of the light 56 may be generated as white light or as specific, discrete wavelengths of light. In certain embodiments, the optical emitter 52 may be a broadband light source configured to emit the light 56 at one or more wavelengths between approximately 500 nm to 650 nm. In such embodiments, the wavelengths of the light 56 may be separated from one another by approximately 5 nm to 10 nm. Thus, in these embodiments, the broadband light source 52 may be configured to emit between approximately 15 to 30 different wavelengths of the light 56. Increasing the number of wavelengths of the light 56 emitted by the broadband light source 52 may reduce an amount of noise in the measurement of the steam quality. In other embodiments, the optical emitter 52 may be a laser source.

As the light 56 is emitted by the broadband light source 52, the light 56 may come in contact with a water drop 58, or droplet. As shown, the water drop 58 may have a generally spherical shape, although other shapes are also possible. The water drop 58 may be carried between the optical emitter 52 and the optical detector 54, and into the light 56, by a flow of steam through an interior of the steam turbine 10. Steam with a lower steam quality may have a greater number of water drops 58 than steam with a high steam quality. That is, the steam quality is defined as the proportion of saturated steam in a saturated water/steam mixture. Thus, a steam quality of 0 indicates 100 percent water, while a steam quality of 1 (or 100 percent) indicates 100 percent steam. The water drop 58 may have a diameter 60, which may be greater than approximately 100 nm, 500 nm, 1000 nm, 2000 nm, 3000 nm, 4000 nm, or 5000 nm. The distribution of diameters 60 in a typical steam turbine 10 may be N-modal, where N=1, 2, 3, 4, or more. For example, in the illustrated embodiment, the distribution of diameters 60 may be bi-model, with small primary water drops 62 and large secondary water drops 64. For example, the diameter 60 of the primary water drops 62 may be between approximately 200 to 1500 nm. The diameter 60 of the secondary water drops 64 may be between 5000 to 10000 nm. The primary water drops 62 may correspond to water drops naturally present in the steam. The secondary water drop 64 may be created by shedding off trailing edges of nozzles and buckets of the steam turbine 10. Thus, the number of primary water drops 62 may be greater than the number of secondary water drops 64. Therefore, in a typical steam turbine 10, the moisture contribution from secondary water drops 64 may be less than the moisture contribution from primary water drops 62.

The light 56 entering the water drop 58 may be transmitted as one or more scattered beams 66. The various scattered beams 66 may not reach the optical detector 54. However, a detected beam 68 may be aligned such that the detected beam 68 is detected by the optical detector 54. An example of an optical detector 54 is a photodetector, which may be configured as a photodiode array. In various embodiments, the photodetector 54 may generate an electrical signal in response to the detected beam 68. In addition, the photodetector 54 may be configured to detect the same range of wavelengths of the light 56 emitted by the broadband light source 52. The detected beam 68 may be less intense than the light 56 because of the scattered beams 66. In other words, because not all of the light 56 reaches the photo detector 54, the detected beam 68 may have a reduced intensity. Thus, in certain implementations, the operation of the steam monitoring system 50 is based on the Mie scattering theory, which represents an analytical solution of Maxwell's equations for the scattering of electromagnetic radiation by spherical particles.

Figure 3:
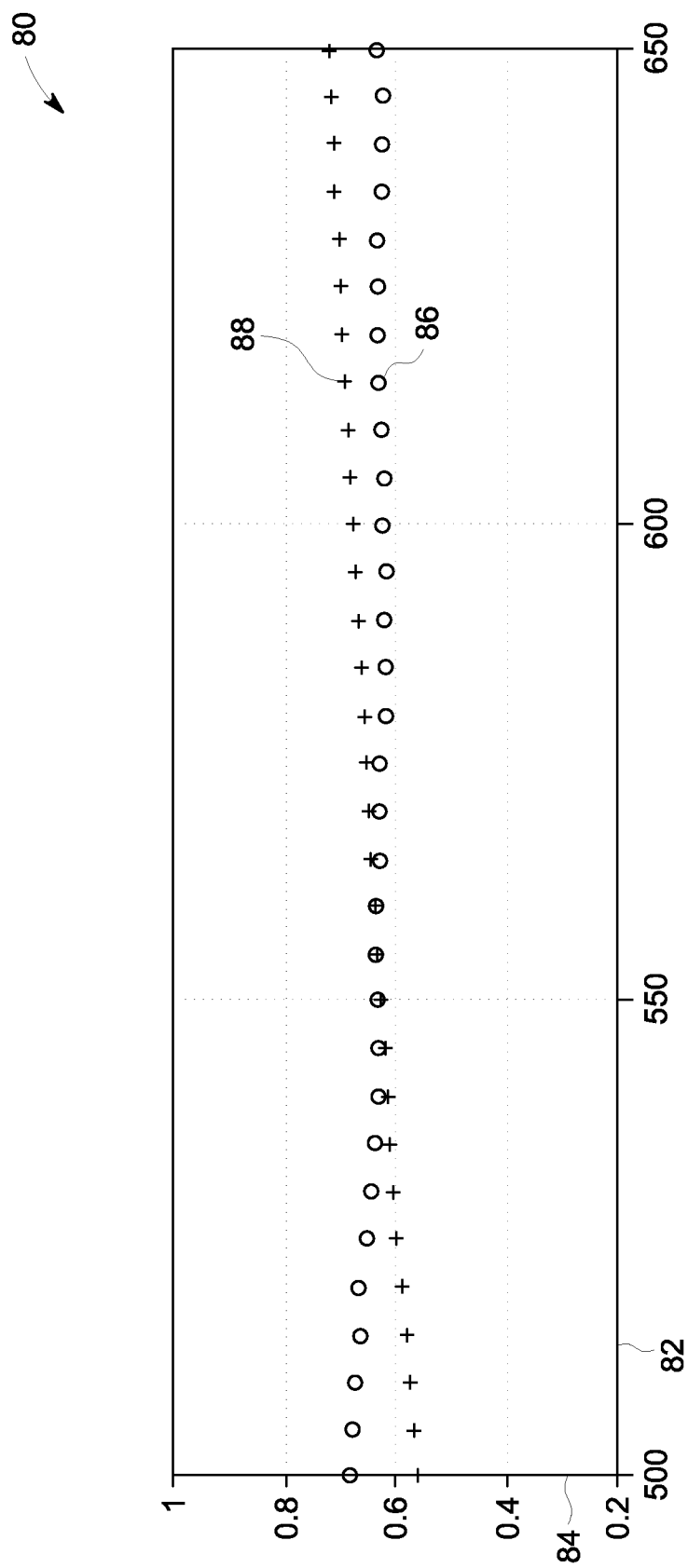
FIG. 3 is a graph showing intensity ratios contaminated by large droplets as a function of wavelength.

FIG. 3 is a graph of intensity ratios showing the effect of attenuation caused by the secondary water drops 64. In the graph 80, the abscissa (x-axis) 82 represents the wavelength of the light 56 emitted by the broadband light source 52 expressed in nanometers. The ordinate (y-axis) 84 represents the intensity ratio, which is defined as the intensity of the detected beam 68 divided by an intensity of the light 56 as would be detected by the photodetector 54 in dry steam (e.g., a steam quality of 1 or 100 percent). In other words, a smaller intensity ratio corresponds to a lower steam quality. Using a typical steam quality monitoring system, the measured intensity ratios 86 at various wavelengths of the light 56 are plotted on the graph 80. Points corresponding to a best fit line 88 through the measured intensity ratios 86 are also plotted on graph 80. As shown, the points corresponding to the best fit line 88 may range from approximately 0.55 to 0.72. However, the actual, or true, intensity ratios based on physical predictions may be greater than those measured by typical steam quality monitoring systems. The discrepancy between the measured intensity ratios 86 and the true intensity ratios may be explained in part by the effect of the secondary water drops 64. Specifically, the secondary water drops 64 may cause greater attenuation of the light 56 than the primary water drops 62. In other words, the effect of the secondary water drops 64 on the attenuation of the light 56 is proportionally greater than the contribution of the secondary water drops 64 to a total moisture content of the steam. Thus, the measured intensity ratios 86 of typical steam quality monitoring systems may be less than those calculated based physical predictions. Additionally, the calculated steam quality based on the measured intensity ratios 86 of typical steam quality monitoring systems may be less than the actual steam quality. Such an inaccurate steam quality may provide an unrealistic view of the conditions inside the steam turbine 10, thereby preventing steps to be taken to improve performance of the steam turbine 10.

Figure 4:
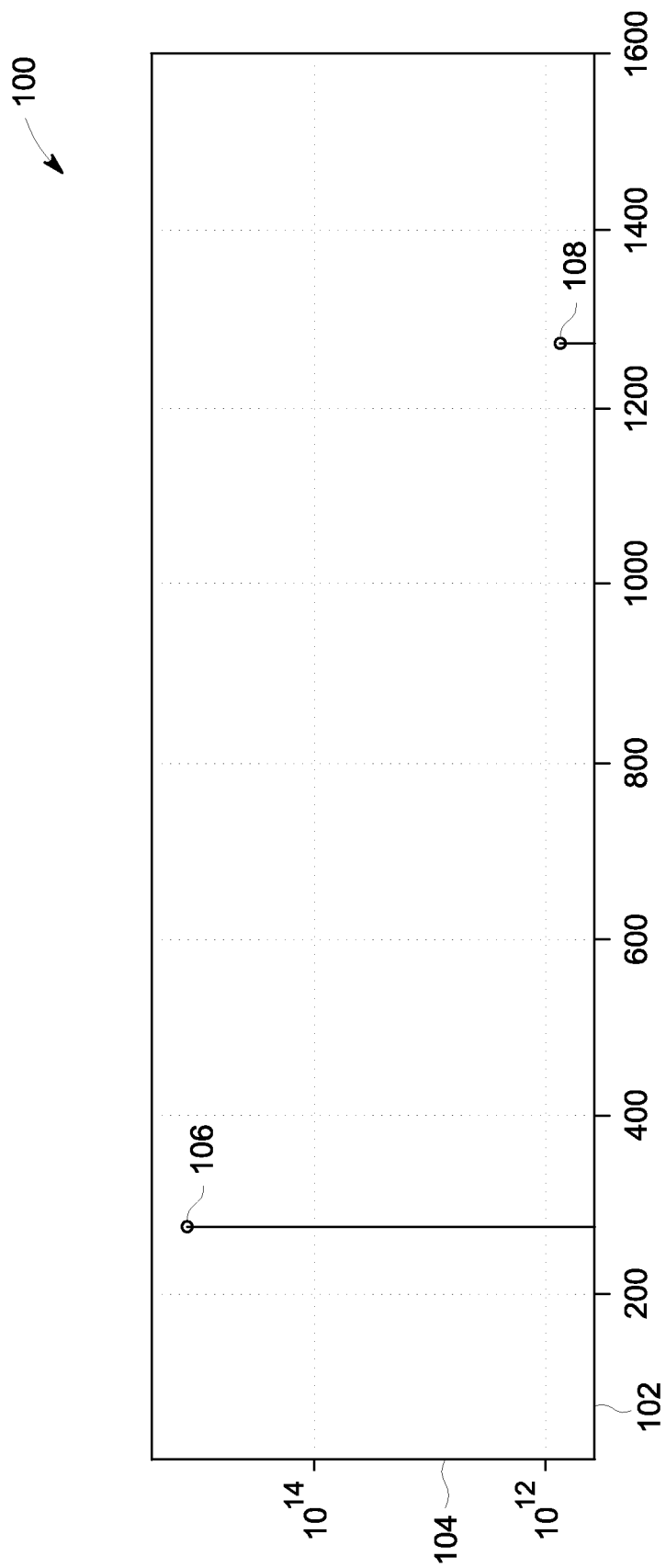
FIG. 4 is a graph showing number densities contaminated by large droplets as a function of diameter.

FIG. 4 is a graph 100 of number densities showing the effect of attenuation caused by the secondary water drops 64. In the graph 100, the abscissa 102 represents the diameter 60 of the water drop 58 expressed in nanometers. The ordinate 104 represents the number density of the water drops 58, which is defined as a number of water drops 58 per unit volume. In the graph 100, the number density is expressed as water drops 58 per cubic meter. The results plotted in the graph 100 are based on the measured intensity ratios 86 shown in FIG. 3. Specifically, the number densities may be calculated from the measured intensity ratios 86 using the equations of the Mie scattering theory. A primary drop density 106 represents the number density of the primary water drops 62, and a secondary drop density 108 represents the number density of the secondary water drops 64. Referring to FIG. 4, the primary drop density 106 is approximately $1.5 \times 10^{15}$ per m$^3$ and the secondary drop density 108 is approximately $9 \times 10^{11}$ per m$^3$. Using these values and the Mie scattering theory, the primary water drops 62 and the secondary water drops 64 appear to contribute to approximately 51 percent and 3 percent of the total moisture content, respectively. Thus, the total moisture content appears to be approximately 54 percent, which is greater than the moisture content based on physical predictions, namely approximately 9 percent.

Figure 5:
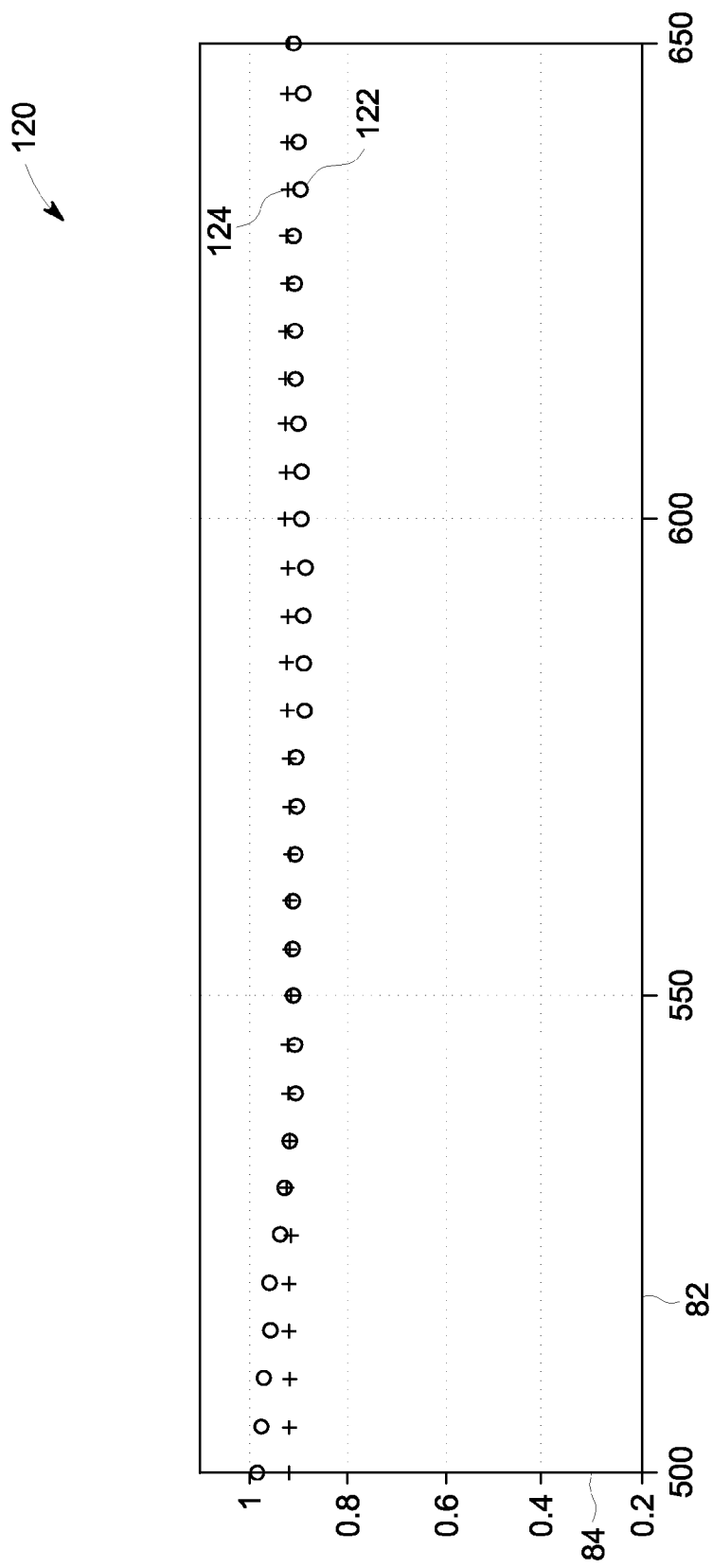
FIG. 5 is a graph showing scaled intensity ratios as function of wavelength, in accordance with an embodiment of the present disclosure.

FIG. 5 is a graph of scaled intensity ratios obtained using the method described in detail below as a function of wavelength. Scaled intensity ratios eliminate or reduce attenuation caused by the secondary water drops 64. The scaled intensity ratios 122 are plotted on graph 120. Points corresponding to a best fit line 124 through the scaled intensity ratios 122 are also plotted on graph 120. As shown, the points corresponding to the best fit line 88 may range from approximately 0.90 to 0.94. Thus, the scaled intensity ratios 122 shown in FIG. 5 are greater than the measured intensity ratios 86 shown in FIG. 3. The scaled intensity ratios 122 are approximately the same as the true intensity ratios based on physical predictions. Specifically, the attenuation caused by the secondary water drops 64 has been removed from the scaled intensity ratios 122. Using accurate steam quality values based on the scaled intensity ratios 122 enables performance of the steam turbine 10 to be improved.

Figure 6:
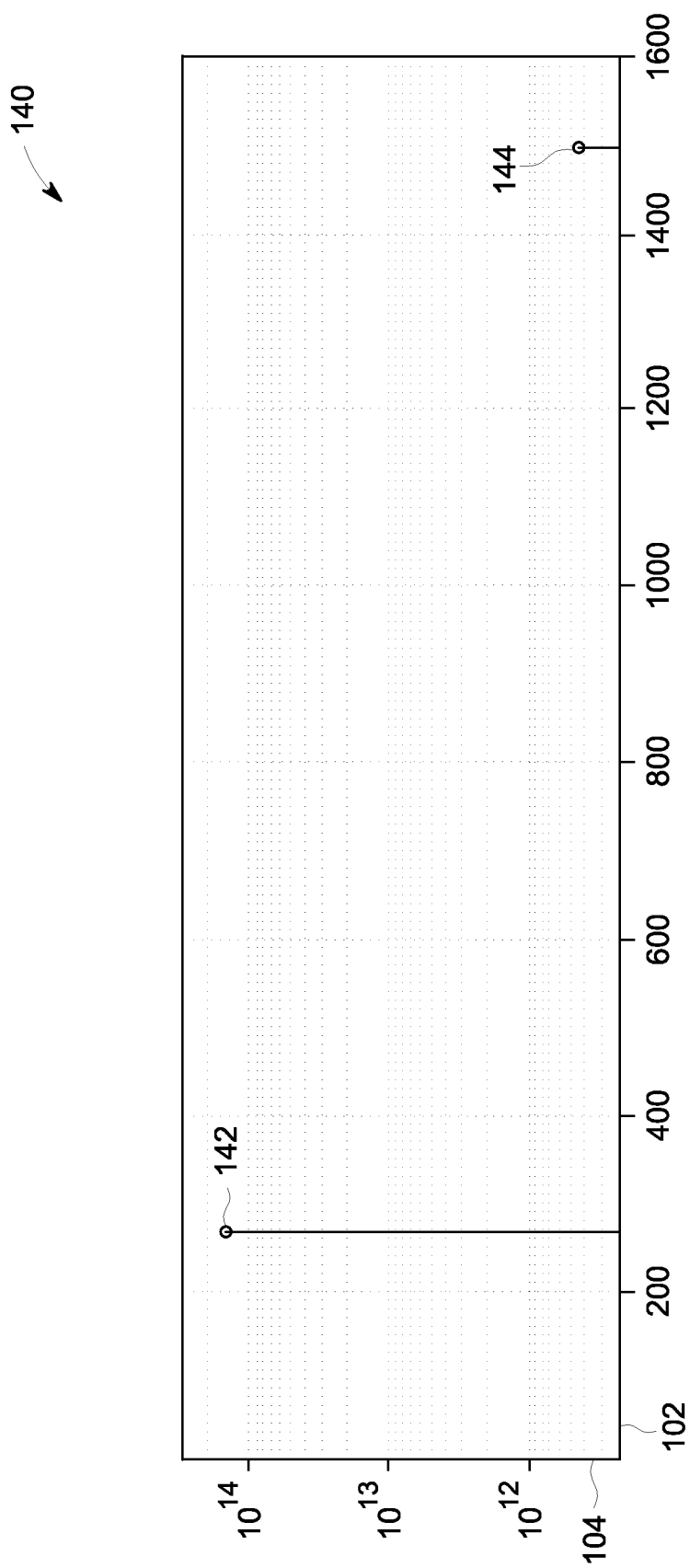
FIG. 6 is a graph showing number densities as a function of diameter, in accordance with an embodiment of the present disclosure.

FIG. 6 is a graph 140 of number densities obtained using the method described in detail below as a function of the diameter 60. The results plotted in the graph 140 are based on the scaled intensity ratios 122 shown in FIG. 5. A correct primary drop density 142 represents the correct number density of the primary water drops 62 and a correct secondary drop density 144 represents the correct number density of the secondary water drops 64. As discussed above, the number densities may be calculated from the scaled intensity ratios 122 using the equations of the Mie scattering theory. Referring to FIG. 6, the correct primary drop density 142 is approximately $1.5 \times 10^{14}$ per m$^3$ and the correct secondary drop density 144 is approximately $5.5 \times 10^{11}$ per m$^3$. Both the correct primary and secondary drop densities 142 and 144 are less than the primary and secondary drop densities 106 and 108 shown in FIG. 4. Using these values and the Mie scattering theory, the primary water drops 62 and the secondary water drops 64 appear to contribute to approximately 6 percent and 3 percent of the total moisture content, respectively. Thus, the total moisture content appears to be approximately 9 percent, which is approximately the same as the moisture content based on physical predictions, namely approximately 9 percent.

Figure 7:
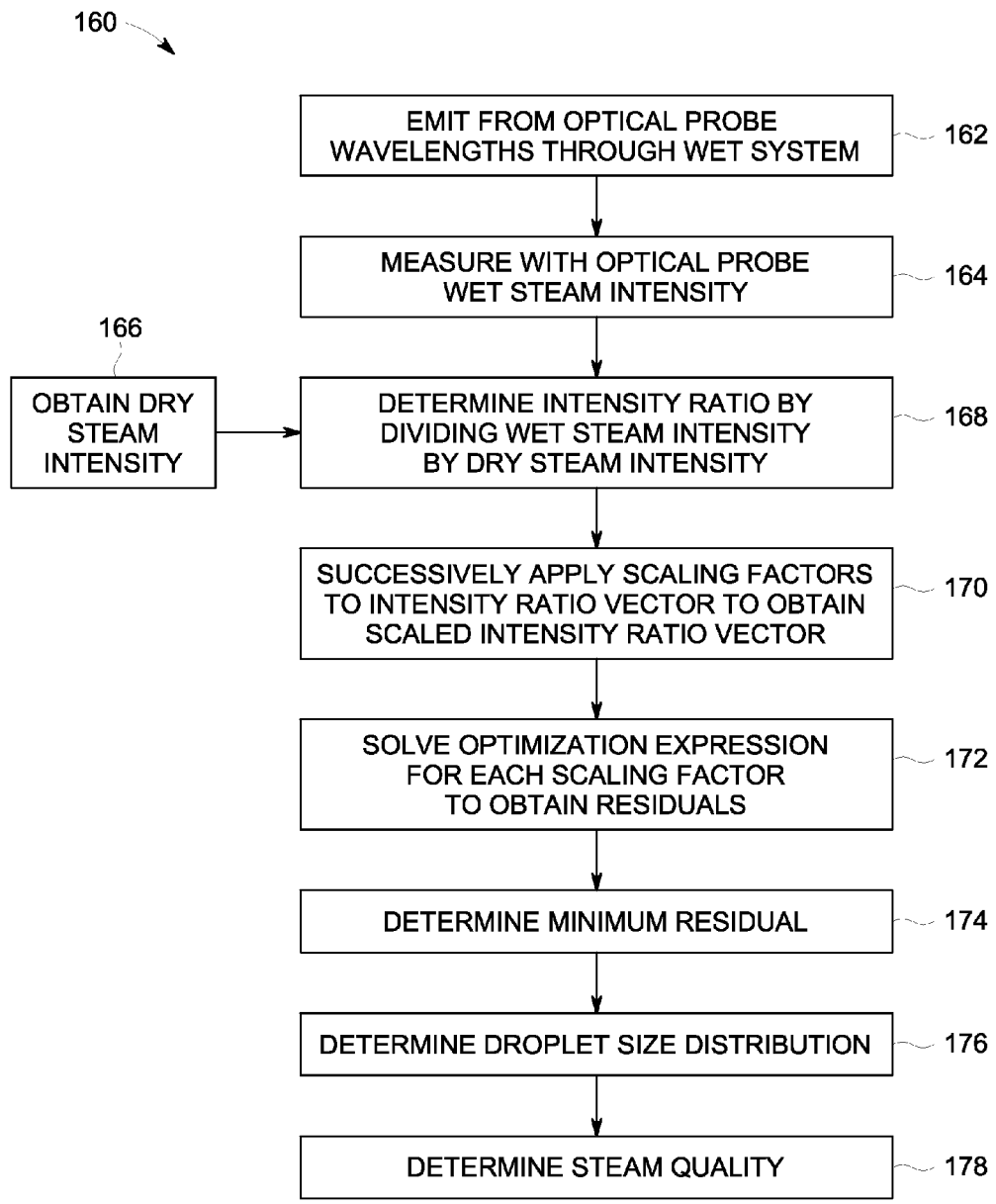
FIG. 7 is a flowchart of a process for determining a steam quality in accordance with an embodiment of the present disclosure.

FIG. 7 is a flow chart 160 of a process for determining the steam quality in the steam turbine 10 using the steam quality monitoring system 50. An embodiment of the invention may be embodied in the form of computer-implemented processes and apparatuses for practicing those processes. Embodiments of the present invention may also be embodied in the form of a computer program product having computer program code containing executable instructions embodied in non-transitory tangible, machine-readable media, such as floppy diskettes, CD-ROMs, hard drives, USB (universal serial bus) drives, or any other computer readable storage medium, wherein, when the computer program code is loaded into and executed by a computer, the computer becomes an apparatus for practicing embodiments of the invention. Embodiments of the invention also may be embodied in the form of computer program code, for example, whether stored in a storage medium, loaded into and/or executed by a computer, or transmitted over some transmission medium, such as over electrical wiring or cabling, through fiber optics, or via wireless transmission, wherein when the computer program code is loaded into and executed by a computer, the computer becomes an apparatus for practicing embodiments of the invention. When implemented on a general-purpose processor, the computer program code segments configure the processor to create specific logic circuits.

Specifically, the steam quality monitoring system 50 may include computer code disposed on a computer-readable storage medium or a process controller that includes such a computer-readable storage medium. The computer code may include instructions for initiating a control function to increase the steam quality if a sensed level is below a threshold level of the steam quality or to notify an operator of the deficient steam quality. In further embodiments, the code may include instructions for measuring the operating variables using process instruments or for cyclically repeating certain instructions.

Returning to FIG. 7, in a step 162, one or more wavelengths $\lambda_i$ of the light 56, up to n wavelengths, are emitted from the optical probe and passed through the wet steam to be monitored. The optical probe may include the broadband light source 52 and the photo detector 54. In a step 164, the optical probe measures a wet steam intensity $I(\lambda_i)$ corresponding to each of the n wavelengths of the light 56 emitted through the wet steam. As discussed in detail above, the measured wet steam intensity may be attenuated as a result of the secondary water drop 64 in the wet steam. In a step 166, the optical probe may obtain a dry steam intensity $I_0(\lambda_i)$ corresponding to each of the n wavelengths of the light 56 emitted through a dry steam. The step 166 may be performed once and the values of the dry steam intensities reused in subsequent calculations. Alternatively, the dry steam intensity values may be derived using physical models or accessed from a local or remote database containing such values, either derived experimentally or using physical models. In a step 168, an intensity ratio vector R is determined by dividing the wet steam intensity $I(\lambda_i)$ by the corresponding dry steam intensity $I_0(\lambda_i)$ for each of the wavelengths of the light 56. For example, an intensity ratio as a function of wavelength $r(\lambda_i)$ may be determined using the following equation:

$$r(\lambda_i) = I(\lambda_i)/I_0(\lambda_i) \quad \text{(Eq. 1)}$$

The n-dimensional vector of intensity ratios R may be formed using the following equation:

$$R = [r(\lambda_1), r(\lambda_2) \ldots, r(\lambda_n)] \quad \text{(Eq. 2)}$$

In a step 170, scaling factors s are successively applied to the intensity ratio vector R to obtain a scaled intensity ratio vector $R_s$, as represented using the following equation:

$$R_s = sR \quad \text{(Eq. 3)}$$

The scaling factors s may be greater than 0 and less than or equal to 1. In a step 172, a suitable value for each of the scaling factors s is calculated to obtain one or more residuals e(s), which may be determined using the following equation:

$$e(s) = \min_{N(D)} \left| R_s - \exp\left( \int_0^{D_{max}} \frac{\pi D^2 l}{4} N(D) E_\lambda(D) \, dD \right) \right| \quad \text{(Eq. 4)}$$

where N(D) is the number density, is a maximum diameter of the drop 58, D is the diameter 60, l is a path length of the drop 58, and $E_\lambda(D)$ is an extinction coefficient. In certain embodiments, the number density N(D) may be constrained. For example, the number density N(D) may be constrained to drops of two diameters, namely primary water drops 62 and secondary water drops 64. In other embodiments, the number density N(D) may be constrained to drops of more than two diameters.

In certain embodiments, the maximum diameter $D_{max}$ may be greater than approximately 1000 nm, 2000 nm, 3000 nm, 4000 nm, or 5000 nm. The path length l is defined as the distance between the broadband light source 52 and the photo detector 54. In addition, the extinction coefficient $E_\lambda(D)$ for drops 58 with diameters 60 greater than approximately 5000 nm is independent of wavelength $\lambda_i$ and diameter D. Thus, the attenuation caused by drops 58 with diameters 60 greater than approximately 5000 nm, such as the secondary water drops 64, is approximately constant. In a step 174, a minimum residual $e_{min}$ of the one or more residuals e(s) determined in the step 172 is determined. In a step 176, the droplet size distribution is determined by calculating the number density N(D) corresponding to the minimum residual $e_{min}$ obtained in the step 174. Finally, in a step 178, the steam quality Y (or wetness fraction) is determined using the following equation:

$$Y = \frac{\pi}{6} \frac{\rho_{water}}{\rho_{steam}} \int_0^{D_{max}} D^3 N(D) \, dD \quad \text{(Eq. 5)}$$

where $\rho_{water}$ is the density of the drops 58 and $\rho_{steam}$ the density of the steam.

This written description uses examples to disclose the invention, including the best mode, and also to enable any person skilled in the art to practice the invention, including making and using any devices or systems and performing any incorporated methods. Further, the representative embodiments provided herein include features that may be combined with one another and with the features of other disclosed embodiments. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of determining a steam quality of a wet steam located in an interior of a steam turbine, the method comprising:
    emitting from an optical probe a plurality of wavelengths through the wet steam;
    measuring with the optical probe a wet steam intensity corresponding to each of the plurality of wavelengths emitted through the wet steam;
    determining an intensity ratio vector by dividing the wet steam intensity by a corresponding dry steam intensity for each of the plurality of wavelengths;
    successively applying scaling factors to the intensity ratio vector to obtain a scaled intensity ratio vector;
    calculating a suitable value for each of the scaling factors to obtain a plurality of residuals;
    determining a minimum residual of the plurality of residuals;
    determining a droplet size distribution by calculating the droplet number density corresponding to the minimum residual; and
    determining the steam quality based on the droplet size distribution.

2. The method of claim 1, wherein the suitable value is based on the function $$e(s) = \min_{N(D)} \left| R_s - \exp\left( \int_0^{D_{max}} \frac{\pi D^2 l}{4} N(D) E_\lambda(D) \, dD \right) \right|$$

where e(s) is the plurality of residuals, N(D) is the droplet number density, $R_s$ is the scaled intensity ratio vector, $D_{max}$ is a maximum droplet size, D is a diameter, l is a path length, and $E_\lambda(D)$ is an extinction coefficient.

3. The method of claim 2, wherein the droplet number density N(D) is constrained to droplets of two diameters.

4. The method of claim 2, wherein the droplet number density N(D) is constrained to droplets of more than two diameters.

5. The method of claim 2, wherein the maximum droplet size $D_{max}$ is greater than approximately 5,000 nanometers.

6. The method of claim 1, wherein the plurality of wavelengths are generated as white light.

7. The method of claim 1, wherein the plurality of wavelengths comprises greater than approximately 15 wavelengths.

8. One or more non-transitory tangible machine-readable media comprising executable instructions, wherein the executable instructions, when executed by a processor, cause the processor to perform acts comprising:
    measuring with an optical probe a wet steam intensity corresponding to each of a plurality of wavelengths emitted through a wet steam;
    determining an intensity ratio vector by dividing the wet steam intensity by a corresponding dry steam intensity for each of the plurality of wavelengths;
    successively applying scaling factors to the intensity ratio vector to obtain a scaled intensity ratio vector;

calculating a suitable value for each of the scaling factors to obtain a plurality of residuals;

determining a minimum residual of the plurality of residuals;

determining a droplet size distribution by calculating the droplet number density corresponding to the minimum residual; and determining a steam quality based on the droplet size distribution.

9. The machine-readable media of claim 8, wherein the suitable value is based on the function $$e(s) = \min_{N(D)} \left| R_s - \exp\left( \int_0^{D_{max}} \frac{\pi D^2 l}{4} N(D) E_\lambda(D) \, dD \right) \right|$$

where e(s) is the plurality of residuals, N(D) is the droplet number density, $R_s$ is the scaled intensity ratio vector, $D_{max}$ is a maximum droplet size, D is a diameter, l is a path length, and $E_\lambda(D)$ is an extinction coefficient.

10. The machine-readable media of claim 9, wherein the droplet number density N(D) is constrained to droplets of two diameters.

11. The machine-readable media of claim 9, wherein the droplet number density N(D) is constrained to droplets of more than two diameters.

12. The machine-readable media of claim 9, wherein the maximum droplet size $D_{max}$ is greater than approximately 5,000 nanometers.

13. The machine-readable media of claim 8, wherein the plurality of wavelengths are generated as white light.

14. A steam quality monitoring system, comprising:

an optical emitter configured to emit light at a plurality of wavelengths;

an optical detector configured to detect light at the plurality of wavelengths;

a processor coupled to the optical emitter and the optical detector, and configured to execute instructions stored in a memory or storage device, wherein the instructions, when executed by the processor, cause the processor to perform acts comprising:

detecting with the optical detector a wet steam intensity corresponding to each of the plurality of wavelengths emitted by the optical emitter through the wet steam;

determining an intensity ratio vector by dividing the wet steam intensity by a corresponding dry steam intensity for each of the plurality of wavelengths;

successively applying scaling factors to the intensity ratio vector to obtain a scaled intensity ratio vector;

calculating a suitable value for each of the scaling factors to obtain a plurality of residuals;

determining a minimum residual of the plurality of residuals;

determining a droplet size distribution by calculating the droplet number density corresponding to the minimum residual; and determining a steam quality based on the droplet size distribution.

15. The steam quality monitoring system of claim 14, comprising a steam turbine, wherein the optical emitter and the optical detector are disposed in an interior of the steam turbine.

16. The steam quality monitoring system of claim 14, comprising a steam quality controller configured to initiate a control function to increase the steam quality if a sensed level is below a threshold level of the steam quality.

17. The steam quality monitoring system of claim 14, wherein the suitable value is based on the function $$e(s) = \min_{N(D)} \left| R_s - \exp\left( \int_0^{D_{max}} \frac{\pi D^2 l}{4} N(D) E_\lambda(D) \, dD \right) \right|$$

where e(s) is the plurality of residuals, N(D) is the droplet number density, $R_s$ is the scaled intensity ratio vector, $D_{max}$ is a maximum droplet size, D is a diameter, l is a path length, and $E_\lambda(D)$ is an extinction coefficient.

18. The steam quality monitoring system of claim 17, wherein the droplet number density N(D) is constrained to droplets of two diameters.

19. The steam quality monitoring system of claim 17, wherein the droplet number density N(D) is constrained to droplets of more than two diameters.

20. The steam quality monitoring system of claim 17, wherein the maximum droplet size $D_{max}$ is greater than approximately 5,000 nanometers.

* * * * *

UNITED STATES PATENT AND TRADEMARK OFFICE
CERTIFICATE OF CORRECTION

PATENT NO. : 8,433,526 B2
APPLICATION NO. : 12/945680
DATED : April 30, 2013
INVENTOR(S) : Roy et al.

Page 1 of 1

It is certified that error appears in the above-identified patent and that said Letters Patent is hereby corrected as shown below:

In the Specification

In Column 7, Line 33, delete "density," and insert -- density, $D_{max}$ --, therefor.

Signed and Sealed this
Eighteenth Day of June, 2013

Teresa Stanek Rea
*Acting Director of the United States Patent and Trademark Office*